United States Patent
Pappe et al.

(10) Patent No.: US 11,631,991 B2
(45) Date of Patent: Apr. 18, 2023

(54) METHOD FOR DISTRIBUTING A LIMITED AMOUNT OF ELECTRICAL POWER FROM AN ENERGY SOURCE

(71) Applicant: Otto Bock Healthcare Products GmbH, Vienna (AT)

(72) Inventors: Alexander Pappe, Vienna (AT); Andreas Weigl-Pollack, Goldgeben (AT); Erik Albrecht-Laatsch, Rosdorf (DE); Michael Nolte, Seeburg (DE); Robert Hoffmann, Vienna (AT); Robert Kaitan, Vienna (AT); Marcus Eder, Vienna (AT); Luis Sagmeister, Pitten (AT); Thomas Pauser, Steinbrunn (AT); Andreas Schramel, Vienna (AT); Daniel Matejcek, Mannswörth (AT)

(73) Assignee: Otto Bock Healthcare Products GmbH, Vienna (AT)

( * ) Notice: Subject to any disclaimer, the term of this patent is extended or adjusted under 35 U.S.C. 154(b) by 150 days.

(21) Appl. No.: 15/733,268

(22) PCT Filed: Dec. 18, 2018

(86) PCT No.: PCT/EP2018/085658
§ 371 (c)(1),
(2) Date: Jun. 18, 2020

(87) PCT Pub. No.: WO2019/121788
PCT Pub. Date: Jun. 27, 2019

(65) Prior Publication Data
US 2020/0306061 A1 Oct. 1, 2020

(30) Foreign Application Priority Data
Dec. 22, 2017 (DE) .................. 10 2017 131 194.7

(51) Int. Cl.
*H02J 1/14* (2006.01)
*H02J 13/00* (2006.01)
(Continued)

(52) U.S. Cl.
CPC .......... *H02J 13/00002* (2020.01); *A61F 2/70* (2013.01); *H02J 1/14* (2013.01);
(Continued)

(58) Field of Classification Search
CPC .................. A61F 2/70; A61F 2002/702; A61F 2002/701; A61F 2002/704; A61F 2/68;
(Continued)

(56) References Cited

U.S. PATENT DOCUMENTS 5,637,933 A * 6/1997 Rawlings ............ H02J 13/0062
340/9.1
10,879,727 B1 * 12/2020 Cooper .................... H02J 9/062
(Continued)

FOREIGN PATENT DOCUMENTS

DE 10 2005 039 886 A1 3/2007
EP 2 709 230 A2 3/2014
EP 3 176 896 A2 6/2017

OTHER PUBLICATIONS

International Search Report for International Application No. PCT/EP2018/085658, dated Apr. 5, 2019, 12 pages.

*Primary Examiner* — Richard Tan
(74) *Attorney, Agent, or Firm* — Holland & Hart LLP

(57) ABSTRACT

A method for distributing a limited amount of electrical power from an energy source to a plurality of electrical loads includes sensing and/or encoding the available electrical power of the energy source, monitoring a power balance of the loads by sensing and/or encoding the drawn power in the individual loads, and reducing the drawn power in the loads
(Continued)

if the available power is not sufficient for supplying all the loads with the required power.

18 Claims, 7 Drawing Sheets

(51) Int. Cl.
*A61F 2/70* (2006.01)
*H02J 7/00* (2006.01)
*H02J 1/10* (2006.01)

(52) U.S. Cl.
CPC .......... *A61F 2002/702* (2013.01); *H02J 1/10* (2013.01); *H02J 7/0063* (2013.01)

(58) Field of Classification Search
CPC ...... H02J 1/14; H02J 7/0063; H02J 13/00002; H02J 1/10

USPC .......................................................... 307/31
See application file for complete search history.

(56) References Cited

U.S. PATENT DOCUMENTS

| | | | |
|---|---|---|---|
| 10,892,618 B1* | 1/2021 | Cooper .................... H02J 9/00 |
| 2003/0144779 A1 | 7/2003 | Obayashi et al. |
| 2003/0151309 A1 | 8/2003 | Hutton |
| 2006/0038577 A1* | 2/2006 | Jang ....................... G11C 5/147 |
| | | | 327/538 |
| 2008/0052544 A1 | 2/2008 | Hsieh et al. |
| 2009/0129032 A1 | 5/2009 | Liedtke et al. |
| 2017/0086671 A1* | 3/2017 | Sessler ................... G16H 40/67 |
| 2018/0145684 A1* | 5/2018 | Chang ................. H03K 17/162 |
| 2018/0205263 A1* | 7/2018 | von Novak, III ......... H02J 7/35 |

* cited by examiner

METHOD FOR DISTRIBUTING A LIMITED AMOUNT OF ELECTRICAL POWER FROM AN ENERGY SOURCE

CROSS REFERENCE TO RELATED APPLICATIONS

This application is a U.S. National Entry and claims priority to PCT International Patent Application No. PCT/EP2018/085658, filed 18 Dec. 2018, and entitled "METHOD FOR DISTRIBUTING A LIMITED AMOUNT OF ELECTRICAL POWER FROM AN ENERGY SOURCE", which claims priority to Germany Patent Application No. 10 2017 131 194.7 filed 22 Dec. 2017, the entire disclosures of which are incorporated herein by this reference.

The invention relates to a method for distributing a limited amount of electrical power from an energy source among a plurality of electrical loads, in particular among loads of an orthopedic system.

TECHNICAL FIELD

Orthopedic components are understood to mean orthoses, prostheses, wheelchairs, data loggers, radio modules, feedback elements, electrical storage devices or parts of orthoses or prostheses or wheelchairs, for example prosthetic joints, prosthetic feet, tube adapters, prosthetic hands, prosthetic elbows, rotation adapters, prosthesis sockets, orthosis splints, orthotic joints, foot shells and sensors connected thereto, storage devices, processors or other data processing devices. A system comprising a plurality of orthopedic components is a combination of such components forming an orthopedic unit which has a functionality extending beyond the functionality of the individual orthopedic component. A system of this type may, for example, be a transfemoral prosthesis consisting of a transfemoral socket, a prosthetic knee joint, a shin tube and a prosthetic foot. A transtibial prosthetic system consists of a transtibial socket and a prosthetic foot connected thereto. Prostheses of an upper extremity as a transhumeral prosthesis can have a socket, an active elbow, a wrist and a gripper. An orthotic system can be designed, for example, as a knee-ankle-foot orthosis.

Orthopedic components are often provided with electrical and/or electronic devices in order to detect, for example, effective forces, spatial positions, torques or assignments of components to one another. In addition, resistances of a damping device can be modified or a motor drive can be activated or deactivated on the basis of determined sensor values which are evaluated in a processor. The usage data of the orthopedic components can be evaluated, for example in order to have a data basis for future settings. In addition, function tests can be carried out by means of connected testing devices. Complete prosthetic arms or orthotic devices, such as computer-controlled arm prostheses or exoskeletons, are required for elaborate restorations.

In the case of complex orthopedic systems, every actuator or electrical load has an energy store assigned to it. In addition, the alignments, for example, of a prosthetic knee joint with an actuatable prosthetic ankle joint are complex and may possibly be performed independently from one another. Even in the case of non-driven components, electronic devices can be provided, for example to measure loads or angular positions via integrated sensors. Due to the modular design and prostheses or orthoses, a multiplicity of different possible combinations exist, which may increase the complexity of a software synchronization or energy supply.

Particularly during stationary operation or during the charging of an energy store within the orthopedic system, the problem can occur that difficulties arise in the distribution of the available electrical power due to the multiplicity of widely differing device combinations and with an increasing energy and power requirement so that a uniform behavior even of different orthopedic systems is guaranteed. Particularly during charging, the power providable by the power supply unit may not be sufficient. Corresponding problems and difficulties such as those which have been described with reference to an orthopedic system are also present in other technical systems with electrical loads.

SUMMARY

The object of the present invention is therefore to provide a method for distributing a limited amount of electrical power with which an overload of an energy source or a power supply unit is prevented without jeopardizing the functionality of the system.

This object is achieved according to the invention by a method with the features disclosed herein. Advantageous embodiments and developments of the invention are disclosed in the description and the figures.

The method for distributing a limited amount of electrical power from an energy source among a plurality of electrical loads of a system provides that the available electrical power of the energy source is first measured and/or coded. A power balance of the electrical loads is monitored by measuring and/or coding the drawn electrical power in the individual loads. If it is established that the available electrical power is not sufficient to supply all loads with the required electrical power, the drawn power is reduced in the loads. For this purpose, it is provided that all loads within the system can reduce their consumption to enable the loads to be operable with a reduced power in order to reduce their consumption, for example to 40% or 50% of the specified maximum power. If the drawn power is reduced in the loads, the entire orthopedic system can continue to be operated, albeit with a restricted performance only, without creating the risk that individual functions can no longer be performed at all. With the method, a uniform power distribution, in particular a uniform distribution of electrical energy among energy stores, is created with which it is possible to supply a plurality of electrical loads with electrical power from an energy source or to supply with energy or charge a plurality of electrical loads or energy stores via a power supply unit. By measuring and coding the available electrical power of the energy source, it is possible to use different power supply units or energy sources of different power classes, since the amount of available electrical power of the energy source is first measured and the drawn power is adjusted depending on the available electrical power. The power drawn from the energy source can be used to perform an action in or on the orthopedic system, e.g. to instigate an adjustment procedure via a motor. Alternatively or additionally, the drawn power can be used to charge one or more energy stores.

The available electrical power energy source can be coded via its voltage characteristic or via a resistance. The energy source can be connected via a plug-in connector or a device connector to the electrical load or the energy store. The ratio between the power available to charge or operate the electrical loads and the required power can be determined via an analog DC voltage via an additional line within the device connector. A voltage value of this DC voltage is defined which signals a full utilization of the energy source to all connected electrical loads. If lower voltages are measured this means that the power intake by the electrical loads must be reduced. It is provided that the voltage value of all electrical loads is measured for this purpose.

The maximum required power of a load can similarly be determined and coded via an electrical resistance. The maximum electrical power intake is calculated via the electrical resistance and the maximum resistance value, wherein the resistance can be calculated from the assumed power of a reference energy source, a resistance at the reference power, the required power, the available power and the available voltage.

The drawn power is advantageously reduced uniformly in all loads so that all loads reduce the drawn power uniformly, for example all loads by 50%. Alternatively, the reduction can be performed individually depending on the requirement of the respective loads, for example by prioritizing the loads which are particularly important for the function and performing a lesser reduction in the drawn power, or by reducing the charging current in individual or all loads. The respective electrical loads can be provided with an identifier or coding which effects a gradation of the reduction among the plurality of electrical loads.

A coding of the available power via analog signals is one possibility for coding the available power in a particularly simple and robust manner. The coding can be performed via a pull-up resistance in a power supply unit or a coding of the maximum power to be drawn via at least one pull-down resistance in at least one load. A pull-down resistor which is connected by a control line to ground is provided for this purpose, wherein the pull-down resistor can optionally be deactivated if, for example, an energy store is not charged via a power supply unit. The coding of the available power via a pull-up resistance provides a resistance in the power supply unit or in the energy source which is forwarded in a control line from the energy source to the device connector. The available supply power can be defined via the pull-up resistance.

Alternatively or additionally, the available power can be coded via digital signals between the energy source and the at least one load, wherein, for example, the loads are connected to a data bus via which the power transmitting to the respective load is transmitted to a control unit and a power balance in all loads can be calculated. The division of the available electrical power which can be distributed among all loads is calculated, e.g. in a computer, in order to infer therefrom how much power can be distributed to the respective load. If an analog and a digital coding are applied simultaneously, it is provided in one development of the invention that the digital coding is prioritized, since digital signals are easier to process in a control unit.

The coding of the available power can be transmitted via an optical medium or wirelessly, so that the drawn power can be adjusted in the case of a wireless coupling also, or independently from a wireless coupling.

One development of the invention provides that the available power is coded in a plug-in connector which connects the load(s) to the energy source, in particular a power supply unit or a battery. Via a plug-in connector or a plug-in connector socket of this type which is assigned to the orthopedic system, a facility exists to define which power is required where and how much energy is fed at what time to which load, independently from the energy source which can be designed as a power supply unit or battery. The plug-in connector or the plug-in connector socket can be provided with a resistor or a circuit board with a corresponding circuit in order to detect, code and, if necessary, reduce the available power as well as the drawn power and also the maximum power to be drawn.

An identifier can be assigned in each case to loads, in particular all loads, wherein all loads of the system provided with an identifier are identified and authenticated. Every identified and authenticated load can be granted a power release which is assigned to it. A power is generally fed from a power supply unit or an energy source to the respective load only following authentication. It is thereby guaranteed that only approved and authenticated electrical loads are usable in the orthopedic system and are supplied with energy. Safety for a user of the orthopedic system is thereby increased, since it is ensured that only tested orthopedic components are used or can be used as part of the orthopedic system.

All components or modules which take in and store or consume energy from the energy source are regarded as loads.

The available electrical power is preferably coded in the energy source.

BRIEF DESCRIPTION OF THE DRAWINGS

An example embodiment of the invention is explained in detail below with reference to the attached figures, in which.

DETAILED DESCRIPTION

Figure 1:
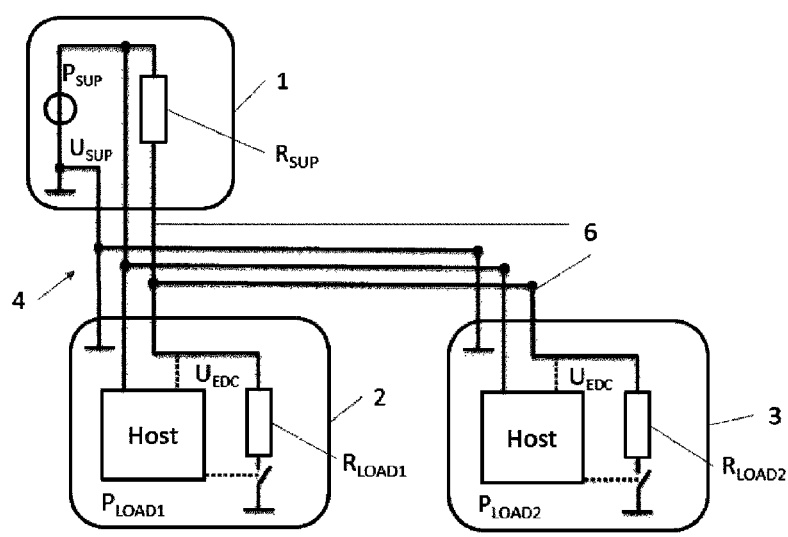
FIG. 1—shows a schematic view of a system with an energy source and two loads.

FIG. 1 shows a schematic view of a power supply unit as the sole energy source 1 to supply a plurality of electrical loads 2 and 3. The power supply unit is connected via a device connector 4 to the first load 2. The second electrical load 3 is similarly connected to the plug-in power supply unit 1 via a cable connection which can similarly be implemented via a plug-in connector 5. The cable connection can also be implemented via the device connector 4 or a further cable connection on the load 2. In the case of a conventional coupling of a power supply unit 1 to a plurality of loads 2, 3, it is problematic to monitor the power $P_{SUP}$ available for charging which can be delivered by the power supply unit 1. Due to installation space restrictions, it may be necessary to provide only one plug-in connection 4 for a power supply unit 1 in a system with a plurality of loads 2, 3. Installation space restrictions apply, for example, in orthopedic systems such as orthoses, prostheses or wheelchairs. In addition, due to a modular design, different device combinations with different loads or energy stores may have to be provided, for example in order to enable an adaptation to the respective customer requirement or to carry out an adaptation to a user through installation of different loads. In addition, an increasing energy and power requirement which was not foreseeable in the original design can occur in the event of developments or in the event of a module exchange. Different electrical energy sources or power supply units with different power classes which are usable for a system may similarly be present. With a rigid definition of available power or maximum power to be delivered, can not possible with a conventional power supply unit and with conventional loads which are supplied with DC voltage via two conductors. It is desirable to provide a system which permits flexibility in terms of modifications both in the hardware and in terms of conditions of use. It is therefore provided according to the invention that, along with the ground and the conductor to the positive pole, a control line 6 via which the power can be coded is provided in both the power supply unit 1 or the energy supply 1 and in the loads 2, 3. The control line 6 or energy distribution line is routed to all plug-in connections 4, 5. The control line 6 indicates the ratio of the power $P_{SUP}$ available for charging to the respectively required power $P_{LOAD1}$, $P_{LOAD2}$ via an analog DC voltage $U_{EDC}$. The voltage value $U_{EDC}$ is therefore the quotient from the power $P_{SUP}$ available for charging and the power $P_{LOAD}$ required in each case on the load 2, 3.

In order to guarantee continuing functional capability for possible extensions or modifications in the system with additional electrical loads or with modified electrical loads or in the event of a combination with other power supply units, it is initially advantageous for the design of the system that a standard power supply unit or a standard energy source with an associated pull-up resistance is defined. All further and future power supply units 1 must be designed as compatible with this standard power supply unit.

It is furthermore advantageous that a voltage value is defined for the DC voltage $U_{EDC}$ with which a full utilization of the respectively connected power supply unit 1 is signaled for all connected devices. If lower voltages $U_{EDC}$ are determined, this means that the respective power intake in the loads 2, 3 must be reduced. The value for the voltage $U_{EDC}$ is measurable in all connected loads 2, 3.

The supply voltage is first defined for the energy distribution control with a uniform charging voltage. If modified charging voltages are required in future, this must be adjusted on the power supply unit side to the respectively defined level.

Figure 2:
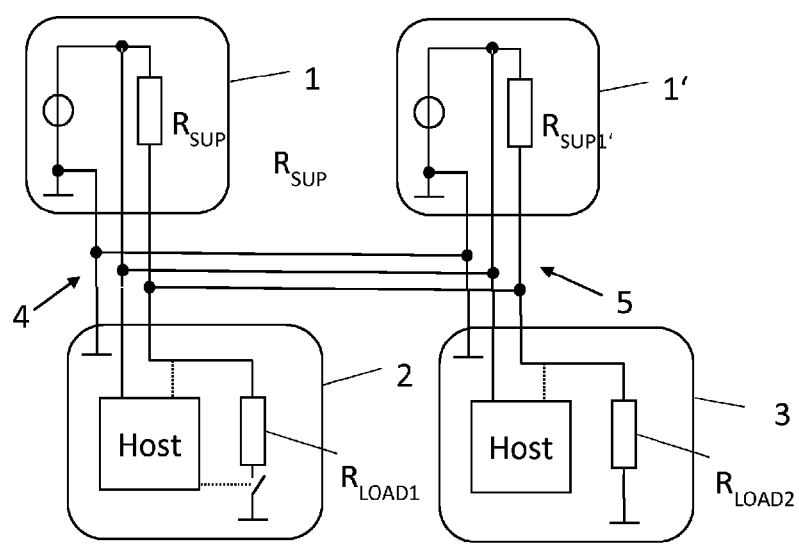
FIG. 2—shows a variant of FIG. 1 with two optional energy sources.

FIG. 2 shows a variant of FIG. 1 in which two different power supply units 1, 1' with different pull-up resistances for different powers are present. The power supply unit 1 has the pull-up resistance $R_{SUP1}$, the second power supply unit 1' has a different pull-up resistance $R_{SUP1'}$, which may, for example, be 50% higher than the pull-up resistance $R_{SUP}$.

Figure 3:
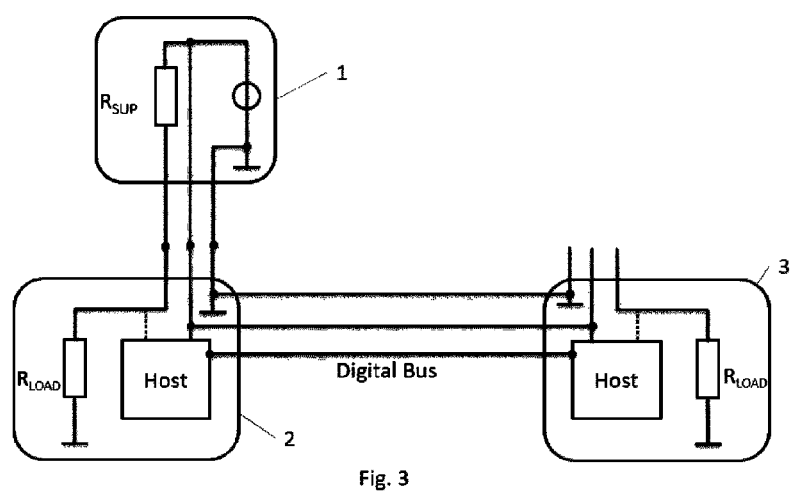
FIG. 3—shows a variant of FIG. 1 with a digital bus as a connection between two loads.

In one example embodiment according to FIG. 3, the available power is coded via digital signals by means of a signal bus, similar to the example embodiments according to FIGS. 1 and 2, but only to a load 2. In addition, a signal exchange takes place between the loads 2, 3. The signal bus is installed between the loads 2, 3. The first load 2 determines how much energy is distributed among the downstream loads 3 and takes over the distribution of the energy within the system, for example an orthosis or prosthesis. It uses the signal bus for this purpose. The pull-down resistances $R_{LOAD}$ in the loads are identical in this example embodiment.

Figure 4:
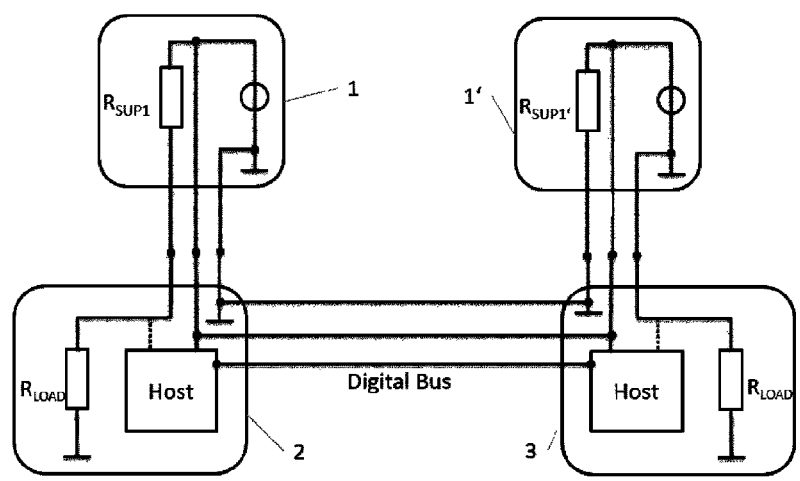
FIG. 4—shows a variant of FIG. 3 with different power supply units.

In FIG. 4, two power supply units 1, 1' are connected in each case to a connection 4 of the respective load 2, 3. When both power supply units 1, 1' are connected, an internal alignment is performed between the loads, 2, 3 in order to determine how the energy from the power supply units 1, 1' is to be distributed among the respective loads.

Figure 5:
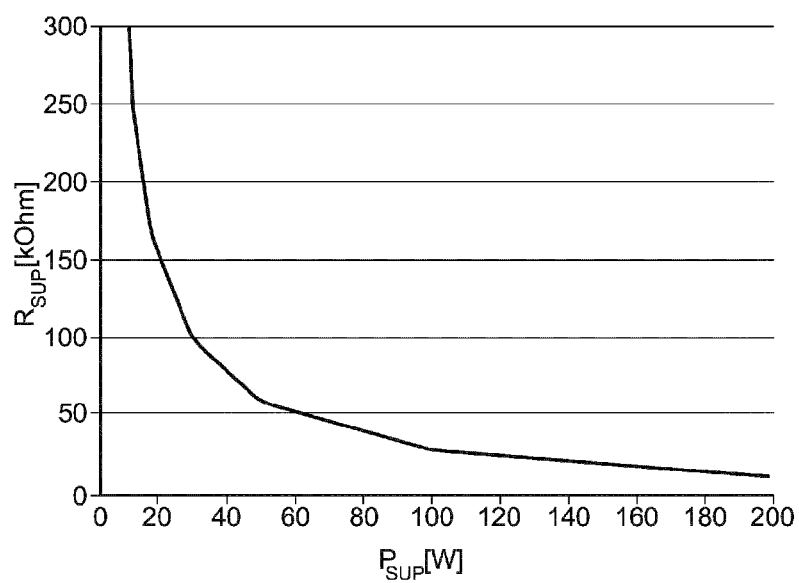
FIG. 5—shows an example dimensioning of a pull-up resistance in a power supply unit.

FIG. 5 shows an example dimensioning of the resistances depending on the available power $P_{SUP}$. All power supply units 1, 1' must implement a pull-up resistance $R_{SUP}$ from the supply voltage $U_{SUP}$ which is present on the control line 6 in order to code the available electrical power $P_{SUP}$ therewith. The necessary minimum value of the respective pull-up resistance is calculated from $$R_{sup_{min}} = R_{Ref}\frac{P_{Ref}}{P_{Sub}},$$

where $P_{Ref}$ is the power of a reference power supply unit and $R_{Ref}$ is the pull-up resistance at a reference power. A possible progression of the ratio of the available power $P_{SUP}$ to the minimum pull-up resistance is plotted in the diagram shown in FIG. 5.

All loads 2, 3 must implement a pull-down resistance $R_{LOAD}$ from the control line 6 to ground in order to code their respective maximum electrical power intake. If the load is not currently being supplied with energy, the pull-down resistance $R_{LOAD}$ can be deactivated, which is indicated by the switch in FIG. 1 and FIG. 2.

The necessary maximum resistance value for the respective pull-down resistance $R_{LOAD}$ is calculated from $$\frac{R_{Ref}P_{Ref}}{P_{LOAD}} \times \frac{U_{100\%}}{U_{SUP} - U_{100\%}}.$$

Figure 6:
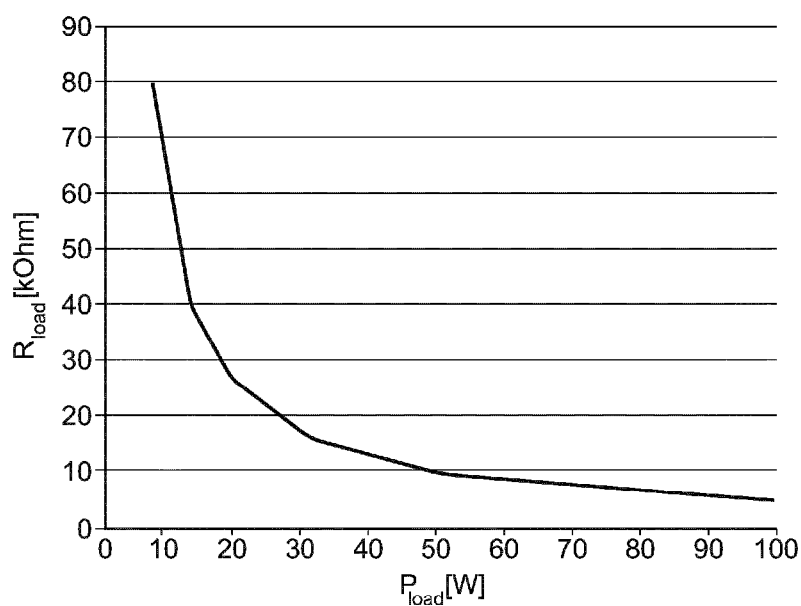
FIG. 6—shows an example dimensioning of a pull-down resistance in loads.

An example curve progression of the ratio between the required power $P_{LOAD}$ and the pull-down resistance $R_{LOAD}$ is shown in the diagram in FIG. 6.

Figure 7:
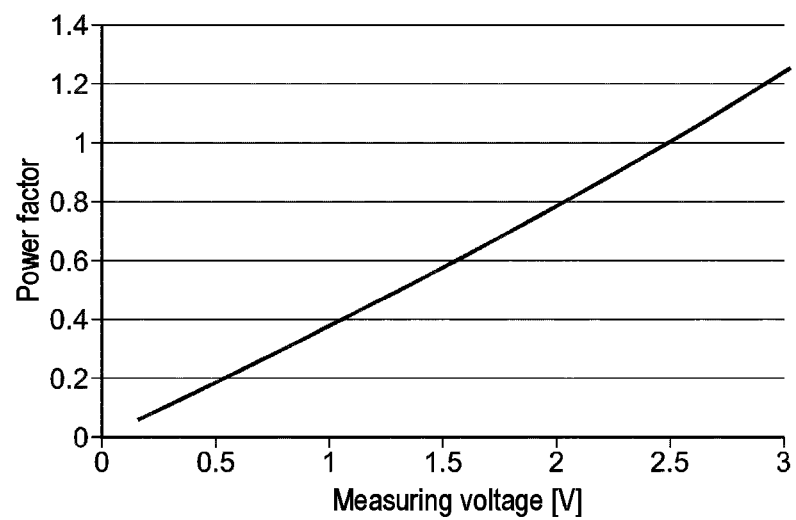
FIG. 7—shows an example calculation of a power factor.

All loads 2, 3 must evaluate the control voltage $U_{EDC}$. If the reference voltage $U_{100\%}$ is not attained, the available electrical power $P_{SUP}$ is less than the required power, so that the respective power intake in the loads 2, 3 must be reduced. The available relative power k is derived from the quotient of the available power $P_{SUP}$ and the sum of the required powers $P_{LOAD}$. If the relative power is above 1, sufficient power is available from the power supply unit 1 or the power supply units 1. If the value for the available relative power k is below 1, too little power is available. A load is permitted to consume at most the proportion of power $P_{max}$ available to it, the maximum available power $P_{max}$ being calculated from the product of the available relative power k and the required power $P_{LOAD}$. The ratio of the measuring voltage $U_{EDC}$ to the power factor k is shown in FIG. 7. In the example calculation, the threshold value for the measuring voltage $U_{EDC}$ is 2.5V in order to ensure that all loads 2, 3 are supplied with sufficient energy.

A status indicator for the available power can be fitted to the respective power supply unit 1, 1'. A coding can be defined for this purpose, for example in three stages corresponding to the power factors. Above the power factor of 1, a green status indicator can signal that sufficient power is available, below the power factor of 0.5, a red status indicator can signal insufficient power, and between them, for example, an amber power indicator can signal that the charging procedure is being extended.

We claim:

1. A method for distributing a limited amount of electrical power from an energy source among a plurality of loads, the method comprising:
    at least one of measuring and coding available electrical power of the energy source;

monitoring a power balance of the plurality of loads by at least one of measuring and coding drawn electrical power in individual loads of the plurality of loads;

reducing the drawn electrical power in the plurality of loads to operate the plurality of loads at reduced power if the available electrical power is not sufficient to supply all of the plurality of loads with a required electrical power, wherein the plurality of loads are connected to a data bus via which the drawn electrical power to the respective load is transmitted to a control unit and a division of the available electrical power among all of the plurality of loads is calculated, wherein the available electrical power is coded via digital signals between the energy source and at least one of the plurality of loads.

2. The method as claimed in claim 1, wherein the available electrical power of the energy source is coded via a voltage characteristic, a resistance, or an analog voltage signal.

3. The method as claimed in claim 1, wherein a maximum required electrical power of at least one of the plurality of loads is determined and coded via an electrical resistance.

4. The method as claimed in claim 1, wherein the reduction is performed uniformly in all of the plurality of loads or is adapted individually to a respective one of the plurality of loads depending on the requirement.

5. The method as claimed in claim 1, wherein the available electrical power is coded via analog signals.

6. The method as claimed in claim 1, wherein the available electrical power is coded via a pull-up resistance in a power supply unit and a maximum electrical power to be drawn is coded via at least one pull-down resistance in at least one of the plurality of loads.

7. The method as claimed in claim 1, wherein, if an analog and digital coding are applied, the digital coding is prioritized.

8. The method as claimed in claim 1, wherein the available electrical power is coded via an optical medium or wirelessly.

9. The method as claimed in claim 1, wherein the available electrical power is coded in a plug-in connector which connects one or more of the plurality of loads to the energy source.

10. The method as claimed in claim 1, wherein an identifier is assigned to the plurality of loads and all of the plurality of loads of the system provided with an identifier are identified and authenticated.

11. The method as claimed in claim 10, wherein each identified and authenticated load of the plurality of loads is granted a power release which is assigned to it.

12. The method as claimed in claim 1, wherein the available electrical power is coded in the energy source.

13. A method for distributing a limited amount of electrical power from an energy source in an orthopedic system among a plurality of loads in the orthopedic system, the method comprising:

at least one of measuring and coding available electrical power of the energy source in the orthopedic system;

monitoring a power balance of the plurality of loads by at least one of measuring and coding drawn electrical power in individual loads of the plurality of loads in the orthopedic system;

reducing the drawn electrical power in the plurality of loads to operate the plurality of loads at reduced power if the available electrical power is not sufficient to supply all of the plurality of loads with a required electrical power for operation of the orthopedic system, wherein the plurality of loads are connected to a data bus via which the drawn electrical power to the respective load is transmitted to a control unit and a division of the available electrical power among all of the plurality of loads is calculated, wherein the available electrical power is coded via digital signals between the energy source and at least one of the plurality of loads.

14. The method as claimed in claim 13, wherein the available electrical power of the energy source is coded via at least one of a voltage characteristic, a resistance, or an analog voltage signal.

15. The method as claimed in claim 13, wherein a maximum required electrical power of at least one of the plurality of loads is determined and coded via an electrical resistance.

16. The method as claimed in claim 13, wherein the reduction is performed uniformly in all of the plurality of loads or is adapted individually to a respective one of the plurality of loads depending on the requirement.

17. The method as claimed in claim 13, wherein the available electrical power is coded via analog signals.

18. The method as claimed in claim 13, wherein the available electrical power is coded via a pull-up resistance in a power supply unit and a maximum electrical power to be drawn is coded via at least one pull-down resistance in at least one of the plurality of loads.

* * * * *